| United States Patent [19] | [11] Patent Number: 4,898,885 |
|---|---|
| Horrobin | [45] Date of Patent: Feb. 6, 1990 |

[54] PHARMACEUTICA AND DIETARY COMPOSITIONS

[75] Inventor: David F. Horrobin, Surrey, England

[73] Assignee: Efamol Limited, Surrey, England

[21] Appl. No.: 232,515

[22] Filed: Aug. 15, 1988

Related U.S. Application Data

[63] Continuation of Ser. No. 833,286, Feb. 27, 1986, abandoned.

[30] Foreign Application Priority Data

Mar. 8, 1985 [GB] United Kingdom ................ 8507058

[51] Int. Cl.$^4$ ............................................. A61K 31/20
[52] U.S. Cl. .................................................... 514/560
[58] Field of Search ........................................ 514/560

[56] References Cited

U.S. PATENT DOCUMENTS

| 4,273,763 | 6/1981 | Horrobin | 424/145 |
| 4,309,415 | 1/1982 | Horrobin | 514/462 |
| 4,386,072 | 5/1983 | Horrobin et al. | 514/560 |
| 4,388,324 | 6/1983 | Horrobin | 514/560 |

FOREIGN PATENT DOCUMENTS 0037175 10/1981 European Pat. Off. ............ 514/560

OTHER PUBLICATIONS

Cecil, Textbook of Medicine, 16th ed., (1982).
Conn's Current Therapy, pp. 552–553, 1986.
Conn's Current Therapy, pp. 534–536, 1984.

*Primary Examiner*—Stanley J. Friedman
*Attorney, Agent, or Firm*—Nixon & Vanderhye

[57] ABSTRACT

A method of treatment of benign prostatic hypertrophy wherein $\gamma$-linolenic acid or dihomo-$\gamma$-linolenic acid or both, as such or in the form of an acceptable and physiologically equivalent derivatives, are administered to a person suffering from the same.

4 Claims, No Drawings

PHARMACEUTICA AND DIETARY COMPOSITIONS

This is a continuation of application Ser. No. 06/833,286, filed Feb. 27, 1986, now abandoned.

FIELD OF THE INVENTION

The invention relates to the treatment of benign prostatic hypertrophy.

GENERAL BACKGROUND

Considerable interest has been shown in recent years in the essential fatty acids, primarily the acids of the n-6 series both as such and in relation to prostaglandin metabolism, but also the acids of the n-3 series.

The n-6 acids in particular are required in the body for the structure of membranes in and around cells, being believed to be necessary in particular for maintaining normal flexibility, fluidity and permeability of such membranes.

The pathways of metabolism of the n-6 essential fatty acids and the related n-3 acids sharing, it is believed, common enzymes in the two pathways, are:

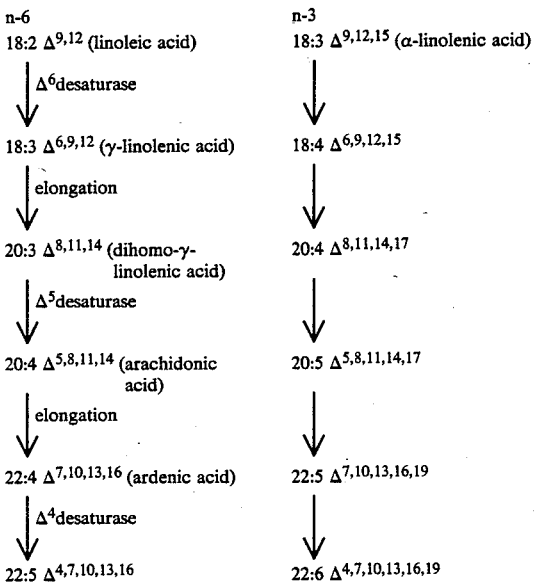

The pathways are not reversible nor, in man, are n-3 and n-6 series acids interconvertible.

These acids, which naturally are of all-cis configuration are systematically named as derivatives of the corresponding octadecanoic, eicosanoic or docosanoic acids e.g. $\Delta^{9,12}$-octadecadienoic acid or $\Delta^{4,7,10,13,16,19}$ docosahexaenoic acid, but the numerical designation such as, correspondingly, 18:2 n-6 or 22:6 n-3 is convenient. Initials, for example, DHA for 22:6 n-3 (docosahexanaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, α-linolenic acid. It was characterised earlier than γ-linolenic acid and reference in the literature simply to linolenic acid, especially in the earlier literature is to the α-acid.

In the body, the n-3 acids are metabolised preferentially and as a result, in plasma for example, levels of α-linolenic acid (18:3 n-3) are low and 18:4 n-3 and 20:4 n-3 are in trace amounts only. In contrast the n-6 acids are normally present in moderate amounts, though γ-linolenic acid (GLA) is at low levels, being apparently converted to dihomo-γ-linolenic acid (DGLA) more rapidly than its relatively slow production from linoleic acid. In both series the elongation stages in the metabolic pathways are much more rapid than the desaturations.

Considering dietary requirements in the n-6 series, it is well known, for example, that linoleic acid cannot be made by the body and so must be taken in the diet. However, it has been generally thought that the body can metabolise linoleic acid to all the other n-6 acids and therefore that provided linoleic acid intake is adequate, no lack of the other n-6 acids will be found. However, in previous patent applications of the present inventor, (for example published European Application No. A 0 003 407, U.S. Pat. No. 4 273 763; published European Patent Application No. A 0 004 770, U.S. Pat. No. 4 309 415; published European Application No. 0 019 423, U.S. Pat. No. 4 388 324) it has been pointed out that this is not so and that the first enzyme in the pathway, the Δ-6 desaturase which, for example, converts linoleic acid to γ-linolenic acid, is not fully effective in a variety of conditions. The administration of γ-linolenic acid or dihomo-γ-linolenic acid or both has been suggested and has been successful in treating a variety of clinical conditions.

PROSTAGLANDINS

In the above patents attention is primarily paid to the function of essential fatty acids in prostaglandin (PG) metabolism and in particular to their role in securing a proper balance between 1-series and 2-series PGs.

For various reasons it is not practical to administer naturally-occurring prostaglandins such as PGE1 and PGE2 to patients. Consequently, considerable attention has focussed on the use of prostaglandin precursors. Conversion of these in the body is believed to be as shown in the following diagram:

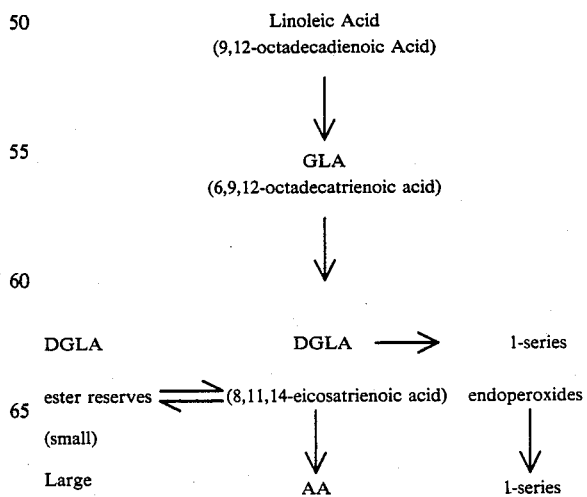

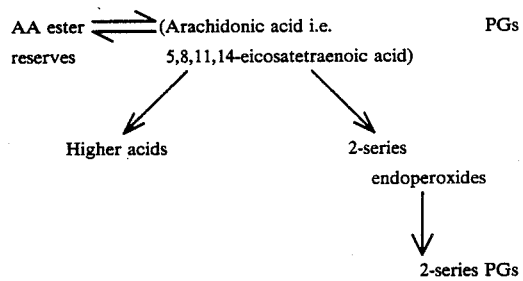

```
AA ester ⇌ (Arachidonic acid i.e.           PGs
reserves      5,8,11,14-eicosatetraenoic acid)
             ↙                    ↘
      Higher acids              2-series
                              endoperoxides
                                    ↓
                                2-series PGs
```

The broad outline of this pathway is well known, and it brings out clearly that a major function of essential fatty acids is to act as precursors for prostaglandins, 1-series PGs being formed from DGLA and 2-series PGs from arachidonic acid. Further, it has recently been found that the 22:4 n-6 acid produced from arachidonic acid gives rise to a series of homo-2-series PGs, though their importance is as yet unknown.

DGLA is the key substance. GLA is almost completely and very rapidly converted in the body to DGLA and so for practical purposes the oral administration of DGLA and GLA amounts to the same thing. DGLA can be converted to a storage form or to PGs of the 1-series or, through arachidonic acid, to PGs of the 2-series.

A balance between 1-series and 2-series PGs is, the inventor believes, highly significant in terms of overall control of the conversion pathway. Such control is not understood in detail but without restriction to the theory it appears first that PGE2 is able to enhance the formation of 1-series PGs, and second that PGE1 is able to block arachidonic acid mobilisation from tissue stores. Thus the conditions for a negative feedback control loop exist; overproduction of PGE2 from arachidonic acid will activate PGE1 synthesis, the PGE1 will inhibit arachidonic acid mobilisation, and production of 2-series PGs will drop. Further, thromboxane A2 (TXA2), an unstable product of the 2-series endoperoxides arising in 2-series PG production, also appears to enhance 1-series PG and in particular PGE1 production. Thus again the activity of the 2-series PG synthesis pathway gives rise indirectly to a material that controls that pathway.

THEORY GENERALLY

Taking the above generally, and without limiting the invention as set out later herein concerning benign prostatic hypertrophy, there are two basic rationales drawing the observations on fatty acids and prostaglandins together.

A. Correction of deficiency. If levels of normal body constituents are below normal in a disease situation then it is a reasonable proposition that those low levels are contributing to and perhaps causing the disease and therefore that they should be corrected.

B. Correction of a 1-series/2-series PG balance. As appears from the earlier patent applications referred to, and from other publications by the inventor, the actions of the 1-series PGs and other metabolic products derived from DGLA are almost all either desirable or neutral, but the actions of the 2-series PGs and other metabolic products derived from arachidonic acid are very mixed, some being desirable and some being highly undesirable.

Now in relation to 1-series/2-series PG balance, studies of the interactions between the metabolism of the n-6 acids and that of the n-3 acids have shown that elongation reactions (e.g. GLA to DGLA) are highly efficient and there is very little competition either way. In contrast, the two series of fatty acids are in competition in the desaturation processes. The n-3 fatty acids interfere with both $\Delta^6$ and $\Delta^5$ desaturation in the n-6 series. This competition occurs even when the n-3 fatty acid is not actually a substrate for the enzyme concerned. For example, 20:5 n-3 competitively inhibits the $\Delta^6$ desaturation forming GLA from linoleic acid. Overall the presence of n-3 fatty acids in a combination leads to inhibition of the conversion of DGLA to arachidonic acid by the $\Delta^5$ desaturase, whence as a result of the presence of n-3 EFAs, the efficiency of either GLA or DGLA is increasing the ratio of DGLA products (1-series PGs) to arachidonic acid products (2-series PGs) is increased.

PROSTATIC HYPERTROPHY

Benign prostatic hypertrophy is a common condition affecting more than 50% of men over the age of 50. There is no medical treatment and surgical excision is eventually required. Apart from the problems caused by the condition itself, there is evidence that those suffering from it are also at increased risk of developing prostatic cancer.

The discovery behind the present invention was made when, in order to treat elevated blood cholesterol levels in a 69 year old man, the inventor administered 3g/day of Evening Primrose Oil containing in total about 2.16g of linoleic acid and 270mg of γ-linolenic acid (GLA). The cholesterol levels can down as expected. However, the man also suffered from benign prostatic hypertrophy with the usual problems of urinary retention, urgency, frequency and nocturia. All of these problems progressively resolved and the man became symptom free. This was a very surprising observation since normally the condition gets progressively worse. The inventor has therefore given Evening Primrose Oil to three other men with similar results, the improvement beginning about three months after starting the Evening Primrose Oil and continuing slowly for some time.

Since there is an abundance of linoleic acid in the diet, and since the amount of linoleic acid in the Evening Primrose oil added only about 15% to the daily intake of this nutrient in the first patient, the inventor concluded that it was the GLA which had brought about the desirable effects. As already discussed, GLA and a range of other biologically active materials are formed from dietary linoleic acid. GLA is very rapidly converted to DGLA in the body and then more slowly to the other materials. The same sequence of enzymes which metabolizes dietary linoleic acid, also metabolizes dietary α-linolenic acid. The ability to convert linoleic acid to GLA (and hence also α-linolenic acid to 18:4 n-3) is known to decrease with age. It is concluded that this decrease has a hitherto quite unexpected effect and that the lack of GLA and its metabolites is a mjaor contributory factor in benign prostatic hypertrophy.

GLA would be expected to be converted along the whole n-6 pathway, through DGLA, but some of the steps are known to be slow even in young people and direct dietary supplementation with one or more of arachidonic acid (20:4 n-6), adrenic acid (22:4 n-6) and 22:5 n-6 will thus be of value. Further, the effect of GLA or DGLA may be enchanced by adding in one or more of the n-3 fatty acids, for the reasons discussed earlier, desirably in that case also with the higher n-6 acids to ensure bodily requirements of them are met.

THE INVENTION

The invention lies in treatment of benign prostatic hypertrophy and compositions when for such treatment, and the preparation of such compositions, wherein the essential is:

1. Use of GLA and/or DGLA;
2. Use in addition to the GLA and/or DGLA, of one or more of the 20:4 n-6, 22:4 n-6 and 22:5 n-6 acids;
3. Use in addition to 1 or 2 of one or more of the 18:3 n-3, 18:4 n-3, 20:4 n-3, 20:5 n-3, 22:5 n-3 and 22:6 n-3 acids.

The dosages of each of the fatty acids are 0.1 mg to 10 g, preferably 30 mg to 600 mg daily, or molar equivalent amounts of glycerides or other derivatives.

The acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemists Society, Champaign, Illinois, U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography on silica gel plates. The phospholipid fraction, taken to reflect essential fatty acid contents most sensitively, is methylated using boron trifluoride-methanol. The resulting methyl esters of the fatty acids are separated and measured using a Hewlett Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of the invention.

DIETARY COMPOSITIONS

The invention is chiefly described in terms of pharmaceutical compositions, but it will be understood that the γ-linolenic and other acids, being in the nature of dietary supplements, could be incorporated in a dietary margarine or other foodstuffs; such foodstuffs possibly containing the other active materials and generally referred to in this description as dietary or pharmaceutical compositions, are within the purview of the invention and thus of the terms pharmaceutical compositions, packs or the like.

FORMS AND SOURCES OF γ-LINOLENIC AND OTHER ACIDS

Convenient physiologically functional derivatives of γ-linolenic acid and dihomo-γ-linolenic acid for use according to the invention, as with the other acids, include salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is however at present convenient to incorporate at least the γ-linolenic acid into compositions in the form of an available oil having a high γ-linolenic acid content, hence references to "oil" herein.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linoleic acid (about 72%) in the form of their glycerides together with other glycerides (percentages based on total fatty acids). Other sources of γ-linolenic acids are Borage species such as Borago officinalis which, though current yield per acre is low, provide a richer source of γ-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| γ-Linolenate | 8.9 |

As preservative, α-tocopherol is added to the oil in a concentration 0.1%.

The seed oil extracts referred to above can be used as such or can, for example, if desired, be fractionated to yield an oily composition containing the triglycerides of γ-linolenic and linoleic as the main fatty acid components, the γ-linolenic acid content being if desired a major proportion. Seed oil extracts appear to have a stabilising effect upon dihomo-γ-linolenic acid if present.

SOURCES OF OTHER ACIDS

All the acids referred to are available. Natural sources of 22:4 and 22:5 n-6 acids, for example, include adrenal glands (22:5) and kidneys (22:4) obtained from slaughter houses. The n-3 acids are, for exmaple, available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

PHARMACEUTICAL PRESENTATION

The compositions according to the invention are conveniently in a form suitable for oral, rectal or parenteral administration in a suitable pharmaceutical vehicle, as discussed in detail for example in Williams British Patent Specification No. 1 082 624, to which reference may be made, and in any case very well known generally for any particular kind of preparation. Thus, for example, tablets, capsules, ingestible liquid or powder preparations can be prepared as required. Injectable solutions of hydrolysed Oenothera oil may be prepared using albumin to solutilise the free acid.

Advantageously, a preservative is incorporated into the preparations. α-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

Soft gelatine capsules made by conventional methods are administered against benign prostatic hypertrophy as follows:

1. 500 mg capsules of Evening Primrose Oil containing 45 mg GLA, 6/day;
2. 500 mg capsules of borage oil containing 90 mg GLA, 4/day;
3. 100 mg capsules of pure GLA, 4/day;
4. 50 mg capsules of pure DGLA, 6/day;
5. Capsules containing 100 mg GLA, 20 mg 20:4 n-6, 50 mg 20:5 n-3, 5/day;
6. Capsules containing 100 mg GLA, 50 mg 22:4 n-6, 50 mg 20:5 n-3, 50 mg 22:6 n-3, 5/day.

An example of a pack as referred to herein comprises 500 mg capsules of Evening Primrose Oil as above, to be taken 6/day, together with capsules of 50 mg each of 20:5 n-3 and 22:6 n-3 to be taken 3/day.

Preparation of compositions as referred to herein is exemplified for example by the preparation of 500 mg capsules of Evening Primrose Oil as above, or for example by addition of 10% by weight of 20:5 n-3 or 22:6 n-3 to Evening Primrose Oil followed by encapsulation.

I claim:

1. A method of treatment of benign prostatic hypertrophy wherein gamma-linolenic acid or dihomo-gamma-linolenic acid or both, as such or in the form of an acceptable and physiologically equivalent derivative, is administered to a person suffering from the same in an amount of 0.1 mg to 10 g of the or each acid, or molar equivalent amounts, of said derivatives, daily.

2. The method according to claim 1, wherein one or more of the 20:4, 22:4 and 22:5 acids of the n-6 series are present also.

3. The method according to claim 1 or 2, wherein one or more of the 18:3, 18:4, 20:4, 20:5 and 22:6 acids of the n-3 series are present also.

4. The method of claim 1, wherein the amounts of fatty acids administered are from 30 mg to 600 mg daily.

* * * * *